Figure 1:
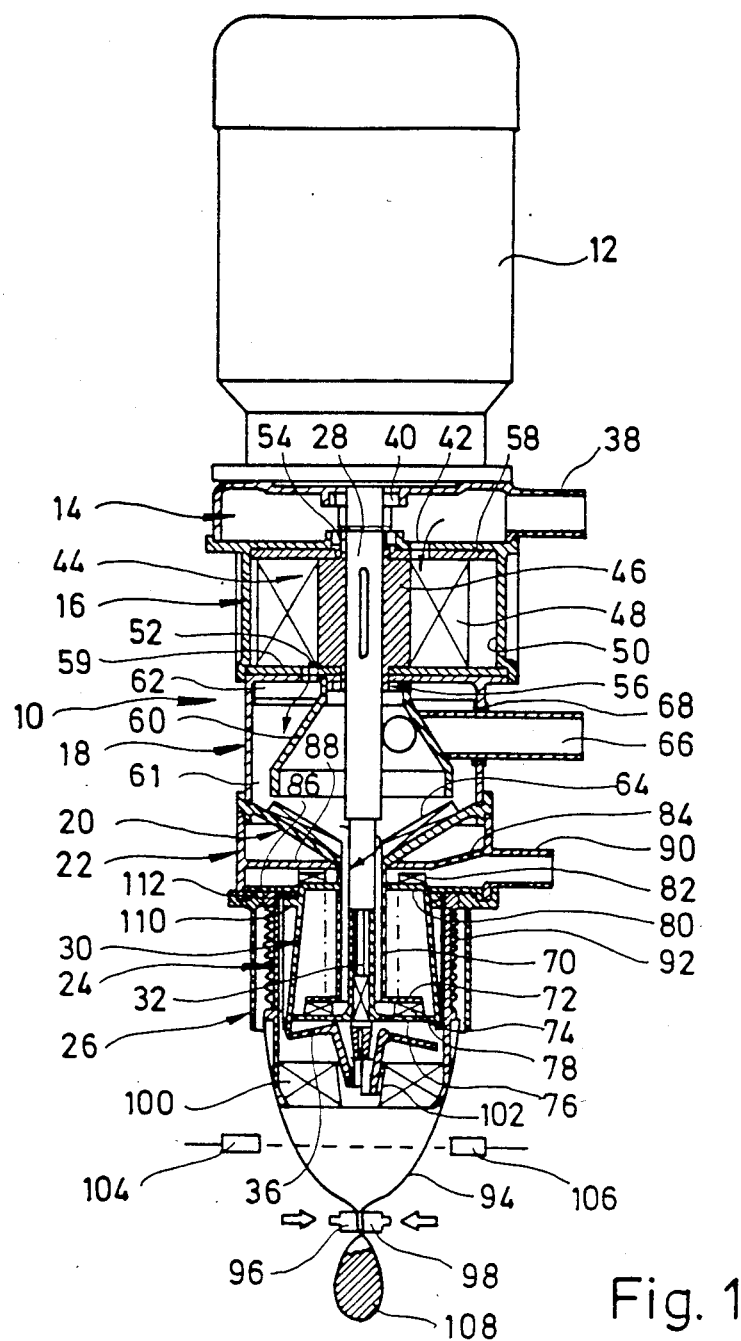

United States Patent [19]

Hofmann et al.

[11] Patent Number: 4,753,632
[45] Date of Patent: Jun. 28, 1988

[54] DEVICE FOR SEPARATING FINE PARTICLES OF SOLID MATTER FROM WASTE FLUID

[75] Inventors: Hans-Joachim Hofmann, Remshalden; Andreas Bollmann, Ingersheim; Walter Dürr, Leonberg, all of Fed. Rep. of Germany

[73] Assignee: Durr Dental GmbH & Co KG, Bietigheim-Bissingen, Fed. Rep. of Germany

[21] Appl. No.: 934,815

[22] Filed: Nov. 25, 1986

[30] Foreign Application Priority Data

Nov. 28, 1985 [DE] Fed. Rep. of Germany ....... 3542133

[51] Int. Cl.$^4$ ............................ B04B 5/10; B04B 7/00
[52] U.S. Cl. .......................................... 494/43; 494/42
[58] Field of Search ................. 494/43, 85, 31, 32, 494/34, 35, 37, 42, 44; 210/781, 782

[56] References Cited

U.S. PATENT DOCUMENTS

| 1,530,758 | 3/1925 | Coleman | 494/44 |
| 1,853,249 | 4/1932 | Ainlay | 494/43 |
| 1,983,701 | 12/1934 | Lewis | 494/43 |
| 3,281,067 | 10/1966 | Beyerle | 494/42 |

FOREIGN PATENT DOCUMENTS 818825 10/1937 France .................. 494/44

Primary Examiner—Robert W. Jenkins
Attorney, Agent, or Firm—Fred Philpitt

[57] ABSTRACT

A device for separating fine particles of solid matter from waste fluid has a water ring pump (16, 44), an air separator (18, 60) and a solid bowl centrifuge (24, 30) which are arranged axially one behind the other in the aforementioned sequence and are driven by the motor shaft (28) of a common drive motor (12).

15 Claims, 2 Drawing Sheets

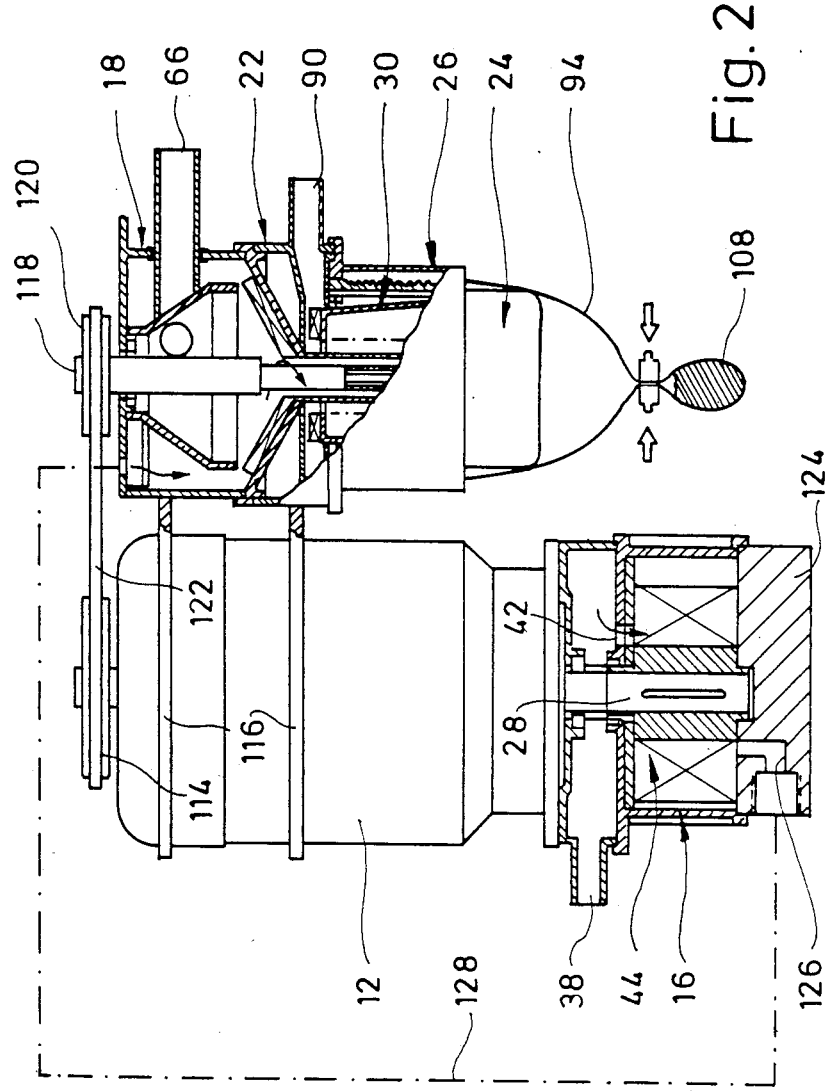

DEVICE FOR SEPARATING FINE PARTICLES OF SOLID MATTER FROM WASTE FLUID

The invention relates to a device for separating fine particles of solid matter, particularly particles of amalgam, from waste fluid in accordance with the opening portion of claim 1.

A known, commercially available device of this type contains a suction pump which first passes waste fluid containing amalgam particles and foam, as produced in a dental practice, through a separator where the air and foam are separated as thoroughly as possible. The waste fluid containing the amalgam particles is then passed to the centrifuge, where the amalgam particles are removed by centrifugal force. After their removal the amalgam particles are collected as a high-particle sludge in a collecting vessel for proper disposal later.

This known device has the drawback of being mechanically complex, since both the suction pump and the drum of the centrifuge need a motor to drive them. Installing the known device is also quite a complicated procedure.

The object of the present invention is to provide a device for separating fine particles of solid matter from waste water that is simple to install and exhibits a single driving motor only.

In accordance with the invention this object is achieved by a device as recited in claim 1.

At the same time the solution offered by the invention ensures that the suction pump cannot be started up when the centrifuge is stationary, which might cause unpurified waste fluid to be forced through the stationary centrifuge drum and into the public drains.

Advantageous embodiments of the invention are indicated in subclaims.

A device in accordance with claim 2 contains no internal hose couplings and is particularly simple to install. Because the water ring pump and the centrifuge are positioned axially one behind the other, it is also possible to pass the streams of fluids between the inlet and outlet of the device through channels in the casing. The result is an inexpensive, compact and reliable device for removing fine particles of solid matter which is very suitable for additional installation in cramped locations such as dental surgeries, which already have to accommodate a variety of equipment.

Since the suction pump incorporated in the separating device of the invention is a water ring pump, an air and foam separator can be connected to it, as stated in claim 3, whereas when a suction pump of the usual type is used it is necessary to interpose such a separator before the suction pump. This allows a suitable separator to be physically positioned between the water ring pump and the centrifuge, thereby achieving separation of the air and foam without increasing the radial dimensions of the device and only slightly increasing its axial dimensions.

The embodiment of the invention in claim 6 enables all the connections to the device to be on one side. This too is an advantage from the point of view of compactness of the whole assembly and straightforward installation of the connectors.

The embodiment of the invention according to claim 7 is advantageous from the point of view of separating the air and foam effectively in the intermediate body of the casing. This also applies to the embodiment of the invention in claim 9.

The advantage of the embodiment of the invention according to claim 13 is that the whole device is low in height. Furthermore, the shaft of the drive motor has only a relatively short overhung section. Lastly, in the device claimed in claim 13 the speed of the centrifuge can be simply selected via the power train by different means than the speed of the water ring pump.

The embodiment of the invention according to claim 14 offers advantages by virtue of its low noise range, and the embodiment according to claim 15 by virtue of the fact that it allows easy transfer of the water being purified from the suction pump to the centrifuge.

The invention is elucidated below with the aid of working examples and with reference to the drawings.

In the drawings:

FIG. 1 is an axial section through a device for separating fine amalgam particles from the waste fluid produced in a dentist's surgery; and FIG. 2 is a side view of a modified device for removing amalgam.

The device for removing amalgam particles illustrated in FIG. 1 has a casing designated overall by 10, which supports an electric drive motor.

Starting at the top of the casing in the drawing, the casing 10 comprises a cup-shaped casing head element 14 which is open at the bottom, a separator casing element 18 which is likewise cup-shaped and open at the bottom, a conical separator base element 20, a cup-shaped centrifuge casing head element 22 which is open at the top, a cylindrical centrifuge casing main element 24, and a protective casing element 26 which encloses the latter coaxially.

As can be seen from the drawing, at their abutment surfaces the various elements of the casing have mating end sections. The various casing elements are extruded plastic parts bonded or welded together.

The motor shaft 28 of the drive motor 12 extends through the various casing elements and at its free end supports a centrifuge drum designated overall by 30. Inside the motor shaft 28 runs a regulating shaft 32, on the end of which a centrifuge drum base 36 is fixed. The latter can be adjusted between a position sealing off the lower end of the drum (shown to the left of the device's axis) and a position uncovering the lower end of the drum (shown to the right of the device's axis), in order to allow amalgam sludge collecting on the peripheral wall of the centrifuge drum 30 to drain at intervals.

The stream of fluid containing amalgam particles, tooth material, dental cement, blood and saliva which is produced in a dental surgery is fed in via an inlet connection 38 supported on the peripheral wall of the cup-shaped casing head element 14. A sliding seal 40 is provided at the base of the casing head element 14 and seals the motor shaft 28 at the point where it enters the casing 10.

Via a radially internal intake 42 provided in the base of the pump casing element 16 the input waste fluid is able to penetrate to the interior of the pump casing element 16, in which a pump impeller 44 supported by the motor shaft 28 turns. The pump impeller exhibits a hub section 46 which is rigidly connected to the motor shaft 28 and a plurality of vanes 48 which project radially from the hub section. As the drawing shows, the axis of the cylindrical inner face 50 of the pump casing element 16 runs parallel to the axis of the motor shaft 28, but is laterally offset relative to the latter—to the right in the drawing. Thus the pump impeller 44 and the pump casing element 16 together form a water ring pump from which the waste fluid can overflow through an opening 52 provided in the base of the separator casing element 18 into the interior of the separator casing element 18. The opening 52 is diametricaly opposite the intake 42 relative to the axis of the motor shaft 28 and like the latter lies adjacent the hub section 46 of the pump impeller 44.

Bearings for the radial extremeties of the pump impeller 44 are designated 54 and 56 in the drawing. At either side of the pump impeller 44 two end plates 58, 59 are rigidly inserted horizontally into the pump casing element 16 and exhibit an opening that is flush with the intake 42 and the opening 52, respectively.

At the base of the cup-shaped separator casing element 18 is suspended an essentially conoid frustum, bell-shaped separator element 60, which is open at its base and together with the peripheral wall of the separator casing element 18 delimits an annular passage 61 for the incoming stream of fluid, which apart from particles of solid matter also contains air and foam. To channel this stream of fluid a guide 62 running in essentially radial direction is provided in the vicinity of the opening 52, said guide 62 being pendent from the base of the separator casing element 18. On the top surface of the conically inclined separator base element 20 are arranged several radial guides 64 distributed in peripheral direction, which break up the rotation of the stream of fluid about the centrifugal axis.

The quantities of air removed from the stream of fluid are trapped inside the bell-shaped separator element 60 and pass from there into an air discharge pipe 66, which passes through the peripheral wall of the separator casing element 18 via a seal 68.

The separator base element 20 is connected to an induction pipe 70 which extends vertically down as far as a guide flange 72, the latter being connected via pump vanes 74 and an impeller flange 76 to the motor shaft. Via a plurality of stays 78 distributed in peripheral direction the impeller flange 76 supports the centrifuge drum 30, which in the drawing expands downward in slightly conical form.

At its top end the centrifuge drum 30 has an end flange 80 which extends radially inward and whose top surface is provided with further pump vanes 82 distributed in peripheral direction.

During operation the water containing particles which has left the separator casing element 18 and entered via the induction pipe 70 is moved rapidly against the peripheral wall of the centrifuge drum 30 by the pump vanes 74. There the solid particles are arrested by the centrifugal force, while the water from which they have been eliminated flows around the end flange 80 into an annular outflow compartment 84. The latter is delimited by a base element 86 of the centrifuge casing head element 22 and is linked to an outlet connection 90 via which the water from which the particles of solid matter have been eliminated is released into the public drains.

As the drawing shows, the inlet connection 38, the air discharge pipe 66 and the outlet connection 90 lie in the same axial plane, so that all the pipe connections can be made from one side of the device. Since the end flange 80 exhibits pump vanes 82, the purified waste fluid can also be conveyed to a waste network connection point lying at some higher level.

As the drawing shows, the main element of the centrifuge casing 24 encloses the centrifuge drum 30 at a small distance and a folded reserve 92 of a tube 94 that can be welded into bags is pushed onto the outer surface of the centrifuge casing main element.

Horizontally below the casing 10 an apparatus for torchcutting the tube 94 is represented diagrammatically as consisting of two welding rods 96, 98 which can be brought toward one another.

When the regulating shaft 32 moves the centrifuge drum base 36 downward in the drawing, by reducing the speed of the motor shaft 28 or cutting the drive motor 12, sludge rich in amalgam particles which had earlier collected on the inner face of the centrifuge drum 30 penetrates to the interior of the tube 94, which has been welded together at its bottom end and is supported by the centrifuge casing main element 24. Smoothing vanes 24 which project radially inward from the bottom end of the centrifuge casing main element 24 and are distributed in peripheral direction assist deposit of the amalgam particles in the interior of the waste collection bag formed by the torch-cut tube 94.

When after discharging a batch of sludge the centrifuge drum base 36 is again moved against the bottom end of the centrifuge drum 30, a central, conical pipe section 102 of the centrifuge drum base 36 sucks excess clear water from inside the tube 94 back inside the centrifuge drum 30, so that the amount of water contained in the tube 94 remains constant for the period of operation but an increasing amount of amalgam collects in the tube 94.

Once a given quantity of amalgam has been collected inside the tube 94, which can for example be monitored by a photoelectric barrier comprising an infrared light emitting diode 104 and an infrared detector 106, the welding rods 96, 98 are moved apart, the tube 94 is pulled vertically downward from the centrifuge casing main element 24, and the tube end containing the amalgam particles is hermetically sealed by bringing together the welding rods 96, 98 and cut off from the tube. At 108 the drawing shows a bag filled with amalgam obtained in this manner.

The reserve 92 is large enough to produce about 6 to 10 of such bags.

In order to prevent fluid from flowing along the outer surface of the centrifuge drum 30 to the outflow compartment 84, at its top end the centrifuge drum 30 supports a radial flange 110 which is equipped with scavenger pump blades 112.

In the separating device shown in FIG. 2 the water ring pump formed by components 14, 16 and 44 is positioned on the drive motor 12, which now has its driving side facing up, and a belt pulley 114 is placed on the upward running second end of the motor shaft 28. The combined air and amalgam separating unit which consists primarily of components 18 and 30 is laterally disposed adjacent the unit formed by the drive motor 12 and the water ring pump, and combined into one unit with the latter, e.g. by connecting plates 116. The top end of the centrifuge shaft 118 which has been brought out of the separating unit supports an additional pulley 120, which is driven via a belt 122 by belt pulley 114. In practice the belt 122 may be a toothed belt, and the two pulleys 114 and 120 can be toothed.

As is evident from FIG. 2, pulley 120 is smaller in diameter than pulley 114, and by this means the centrifuge drum 30 is made to resolve at a higher speed than the water ring pump.

Water is transferred from the outlet of the water ring pump to the separator unit via a base element 124 of the water ring pump, said base element exhibiting a radial transfer duct 126, which leads via a pipe 128 to the separator casing element 18.

The mode of operation of the device illustrated in FIG. 2 is similar to that of the device in FIG. 1; as can be seen from FIG. 2, this device is, however, particularly low in height, and the resolving shafts have only short overhung sections.

We claim:

1. A device for separating fine particles of solid matter, particularly amalgam particles, from waste fluid, having a motor, a solid bowl centrifuge drum driven by the motor shaft, a collecting vessel for particle sludge which can be connected to the interior of the centrifuge drum, and a casing enclosing the drum and incorporating an inflow compartment for contaminated water and an outflow compartment for purified water, characterized in that the motor shaft (28) additionally supports a water ring pump impeller (44) enclosed by a pump casing element (16), the axis of the inner wall (50) of the pump casing element (16) running parallel to the axis of the motor shaft (28) but laterally offset relative thereto; that the inflow compartment (14) adjoins the pump casing element (16) and is connected to the intake of the water ring pump formed by the pump casing element (16) and the pump impeller (44); and that the outlet of the water ring pump (16, 44) is connected to an induction pipe (70) which projects into the interior of the centrifuge drum (30).

2. The device of claim 1, characterized in that the outlet of the water ring pump (16, 44) is connected to the induction pipe (70) via an intermediate casing element (18).

3. The device of claim 2, characterized in that the intake (42) of the water ring pump is provided in an end wall of the pump casing element (16) and the inflow compartment is delimited by a cup-shaped casing head element (14) positioned on said end wall, the casing head element supporting an inlet connection (38) on its peripheral wall.

4. The device of claim 3, characterized in that the outlet opening (52) of the water ring pump (16, 44) is provided in the second end wall of the pump casing element (16) opposite the intake (42) relative to the axis of the pump.

5. The device of claim 3, characterized in that the annular outflow compartment (84) is delimited by a centrifuge casing head element (22) whose peripheral wall is provided with an outflow connection (82) which lies in the same axial plane of the device as the inlet connection (38) and the air discharge pipe (66).

6. The device of claim 3, characterized in that the water ring pump (16, 44) is disposed adjacent the drive motor (12) and the centrifuge drum (30) is arranged at the free end of the motor shaft (28) and that the casing head element (14) exhibits a seal (40) for the motor shaft (28).

7. The device of claim 2, characterized in that the intermediate element of the casing (18) exhibits a bell-shaped separator element (60) which is adjacent the pump casing element (16), closed toward the pump casing element (16) and open at the other end, and the interior of which is connected to an air discharge pipe (66) which is fed, tightly sealed, through the peripheral wall of the casing intermediate element (18).

8. The device of claim 7, characterized by a radial guide (62) for channeling the stream of fluid entering the casing intermediate element (18).

9. The device of claim 7, wherein the motor shaft (28) is vertically aligned, characterized in that the base (20) of the casing intermediate element (18) conically decreases in size toward its center.

10. The device of claim 7, characterized by radial guides (64) supported by the base (20) of the casing intermediate element (18) to smoothe the stream of fluid leaving the casing intermediate element (18).

11. The device of claim 2, characterized in that each of the various casing elements (14 - 26) is cup-shaped and their cylindrical peripheral walls have essentially the same radius, the free end of the peripheral wall of one cup-shaped casing element in each case being hermetically connected to the base of a neighboring casing element.

12. The device of claim 11, characterized in that the casing elements are extruded from plastic.

13. The device of claim 1, characterized in that the centrifuge drum (30) is laterally disposed next to the drive motor (12) and set in rotational motion by the motor shaft via a power train (114, 120, 122).

14. The device of claim 13, characterized in that the power train (114, 120, 122) comprises a belt drive, preferably a toothed belt drive.

15. The device of claim 13, characterized in that the water ring pump is disposed on the top surface of the drive motor.

* * * * *